(12) United States Patent
Umezawa et al.

(10) Patent No.: US 12,229,225 B2
(45) Date of Patent: Feb. 18, 2025

(54) INFORMATION PROCESSING SYSTEM, INFORMATION PROCESSING APPARATUS, INFORMATION PROCESSING METHOD, AND NON-TRANSITORY STORAGE MEDIUM

(71) Applicant: CANON KABUSHIKI KAISHA, Tokyo (JP)

(72) Inventors: Kohtaro Umezawa, Tokyo (JP); Ryuta Ueda, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 693 days.

(21) Appl. No.: 17/493,362

(22) Filed: Oct. 4, 2021

(65) Prior Publication Data

US 2022/0108124 A1 Apr. 7, 2022

(30) Foreign Application Priority Data

Oct. 6, 2020 (JP) .................................. 2020-169032

(51) Int. Cl.
| | |
|---|---|
| *G06F 18/2431* | (2023.01) |
| *A61B 5/00* | (2006.01) |
| *G06F 18/20* | (2023.01) |
| *G06F 18/40* | (2023.01) |
| *G16H 30/20* | (2018.01) |
| *G16H 50/70* | (2018.01) |

(52) U.S. Cl.
CPC ........ *G06F 18/2431* (2023.01); *A61B 5/7267* (2013.01); *G06F 18/285* (2023.01); *G06F 18/40* (2023.01); *G16H 30/20* (2018.01); *G16H 50/70* (2018.01); *A61B 2576/00* (2013.01); *G06V 2201/03* (2022.01)

(58) Field of Classification Search
CPC .... G06F 18/2431; G06F 18/285; G06F 18/40; G16H 30/20; G16H 50/70; A61B 5/7267
See application file for complete search history.

(56) References Cited

U.S. PATENT DOCUMENTS

| | | | |
|---|---|---|---|
| 10,963,788 B1 * | 3/2021 | Parker | G06N 20/00 |
| 2018/0181875 A1 * | 6/2018 | Motohashi | G06Q 30/0283 |
| 2018/0240551 A1 * | 8/2018 | Perrey | G16H 30/40 |
| 2019/0316209 A1 * | 10/2019 | Hubbell | C12Q 1/6806 |

(Continued)

FOREIGN PATENT DOCUMENTS

| | | |
|---|---|---|
| JP | 2019075159 A | 5/2019 |
| JP | 2020042810 A | 3/2020 |

*Primary Examiner* — David Bilodeau
(74) *Attorney, Agent, or Firm* — Canon U.S.A., Inc. IP Division

(57) ABSTRACT

An information processing apparatus according to an exemplary embodiment of the present disclosure includes a storage unit configured to store a plurality of trained models including a first trained model for classifying medical image data into a class belonging to a first class hierarchy, and a second trained model for classifying the medical image data into a class belonging to a second class hierarchy lower than the first class hierarchy, an acquisition unit configured to acquire information about inference, a selection unit configured to select a plurality of trained models having a hierarchical relationship from among the stored plurality of trained models, based on the acquired information about inference, and a notification unit configured to provide a notification of the selected plurality of trained models.

20 Claims, 8 Drawing Sheets

(56) References Cited

U.S. PATENT DOCUMENTS

| | | | |
|---|---|---|---|
| 2020/0012935 A1* | 1/2020 | Goodsitt | G06T 7/194 |
| 2020/0193595 A1* | 6/2020 | Iwamura | G16H 10/60 |
| 2021/0133976 A1* | 5/2021 | Carmi | G16H 30/20 |
| 2021/0279525 A1* | 9/2021 | Goyal | G06V 10/776 |
| 2021/0295103 A1* | 9/2021 | Tanniru | G06V 10/7747 |
| 2022/0020142 A1* | 1/2022 | Anderson | G06N 3/084 |

* cited by examiner

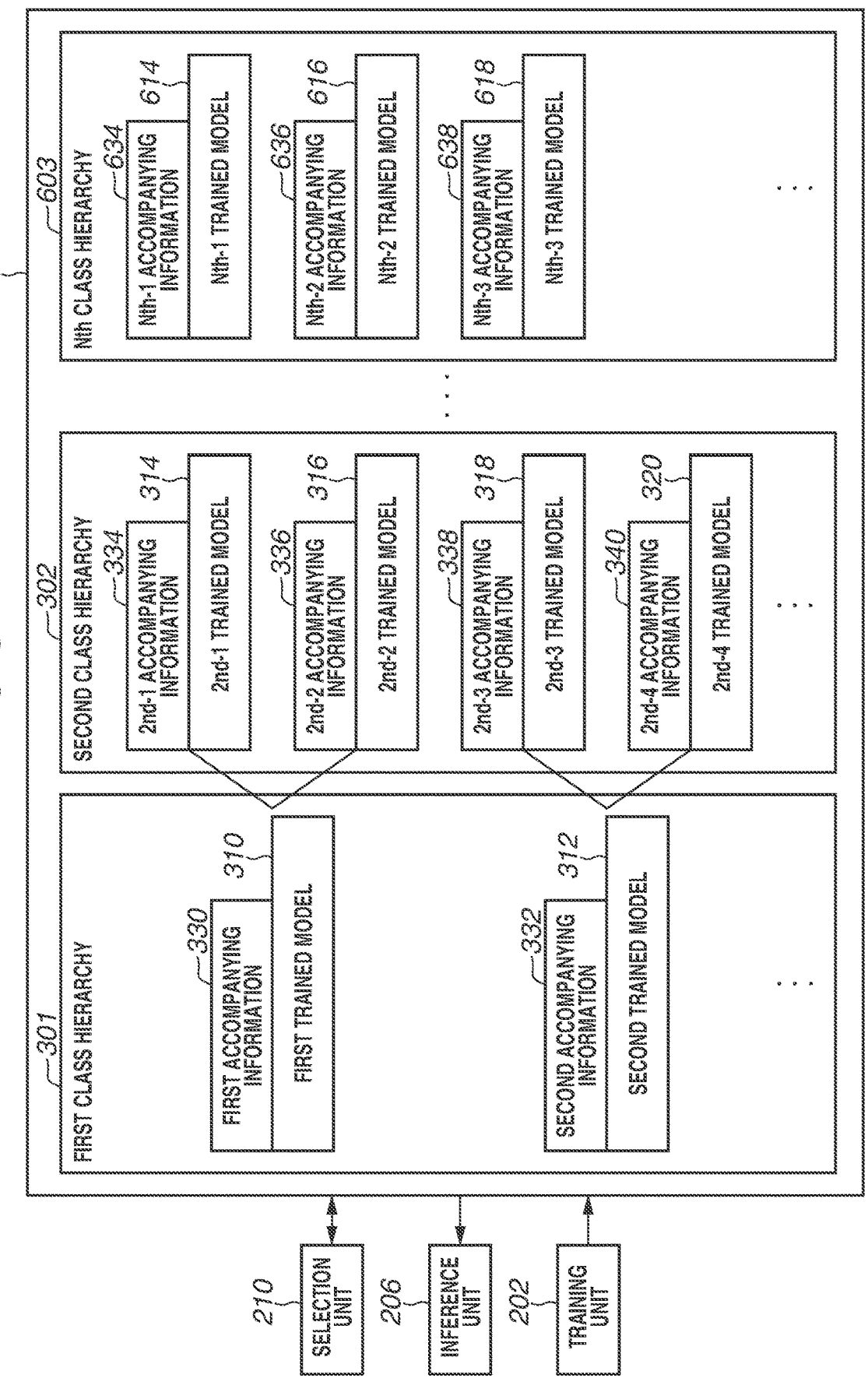

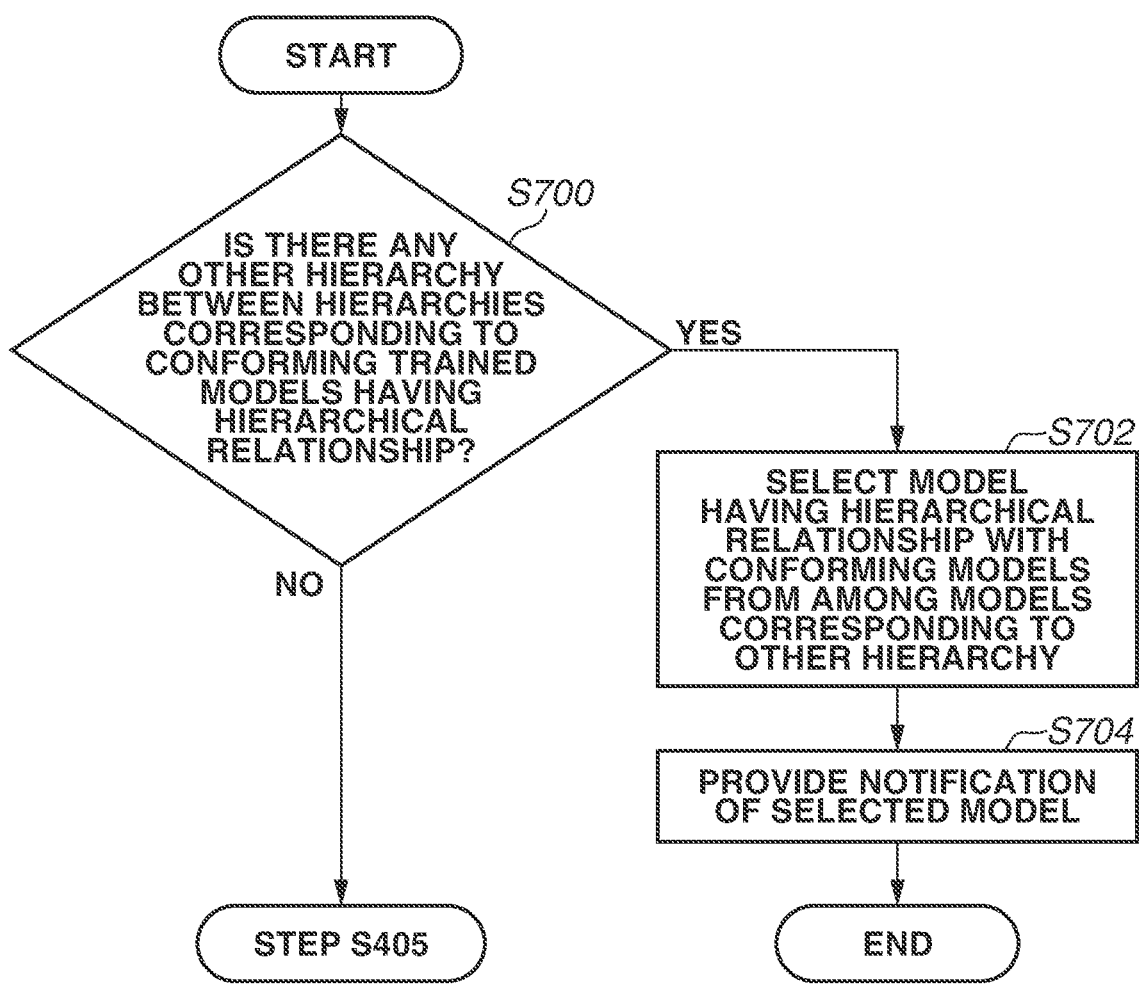

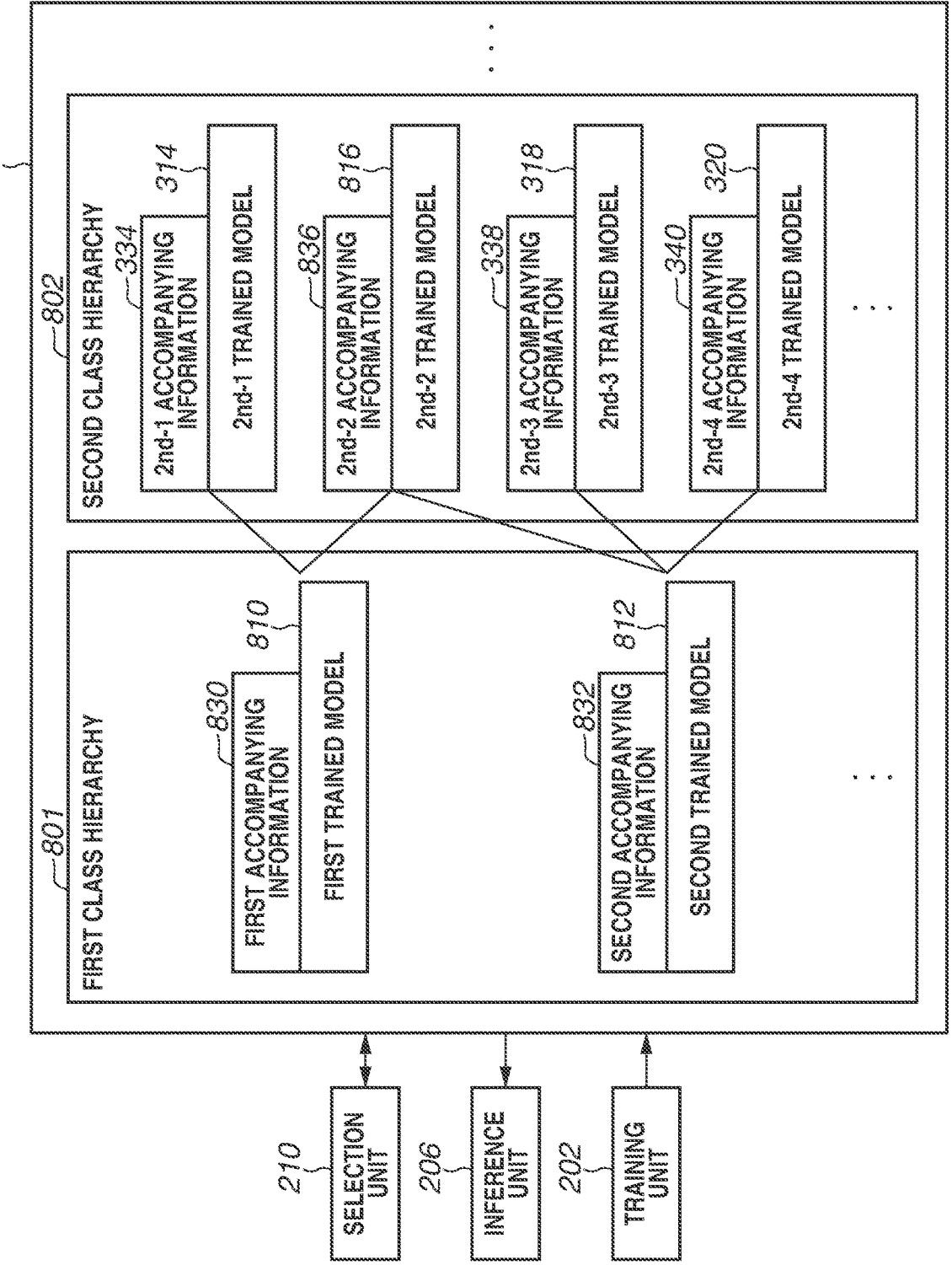

INFORMATION PROCESSING SYSTEM, INFORMATION PROCESSING APPARATUS, INFORMATION PROCESSING METHOD, AND NON-TRANSITORY STORAGE MEDIUM

BACKGROUND

Field of the Disclosure

The present disclosure relates to an information processing system, an information processing apparatus, an information processing method, and a storage medium for performing inference using a plurality of trained models.

Description of the Related Art

There is known a computer aided diagnosis (CAD) system that analyzes medical data acquired by a medical imaging apparatus and provides diagnosis support information to doctors. The CAD system applies a machine training technique to, for example, medical image data included in medical data, and outputs diagnosis support information.

Japanese Patent Application Laid-Open No. 2020-42810 discusses a technique for enhancing the reliability of analysis based on machine training. In this technique, at least one of different image capturing methods and different signal processes is performed to acquire a plurality of processed medical signals for a subject, and inference is performed using a plurality of trained models for each of the plurality of processed medical signals.

SUMMARY

The present disclosure is directed to providing an information processing system, an information processing apparatus, an information processing method, and a storage medium for selecting a plurality of trained models having a hierarchical relationship.

According to an aspect of the present disclosure, an information processing apparatus includes a storage unit configured to store a plurality of trained models including a first trained model for classifying medical image data into a class belonging to a first class hierarchy, and a second trained model for classifying the medical image data into a class belonging to a second class hierarchy lower than the first class hierarchy, an acquisition unit configured to acquire information about inference, a selection unit configured to select a plurality of trained models having a hierarchical relationship from among the stored plurality of trained models, based on the acquired information about inference, and a notification unit configured to provide a notification of the selected plurality of trained models.

Further features of the present disclosure will become apparent from the following description of exemplary embodiments with reference to the attached drawings.

BRIEF DESCRIPTION OF THE DRAWINGS

FIG. 6 is a block diagram illustrating a configuration of a storage unit in an information processing apparatus according to a second exemplary embodiment of the present disclosure.

FIG. 7 is a flowchart illustrating trained model selection processing according to the second exemplary embodiment.

FIG. 8 is a block diagram illustrating a configuration of a storage unit in an information processing apparatus according to a fourth exemplary embodiment of the present disclosure.

DESCRIPTION OF THE EMBODIMENTS

Exemplary embodiments of the present disclosure will be described below with reference to the accompanying drawings.

Figure 1:
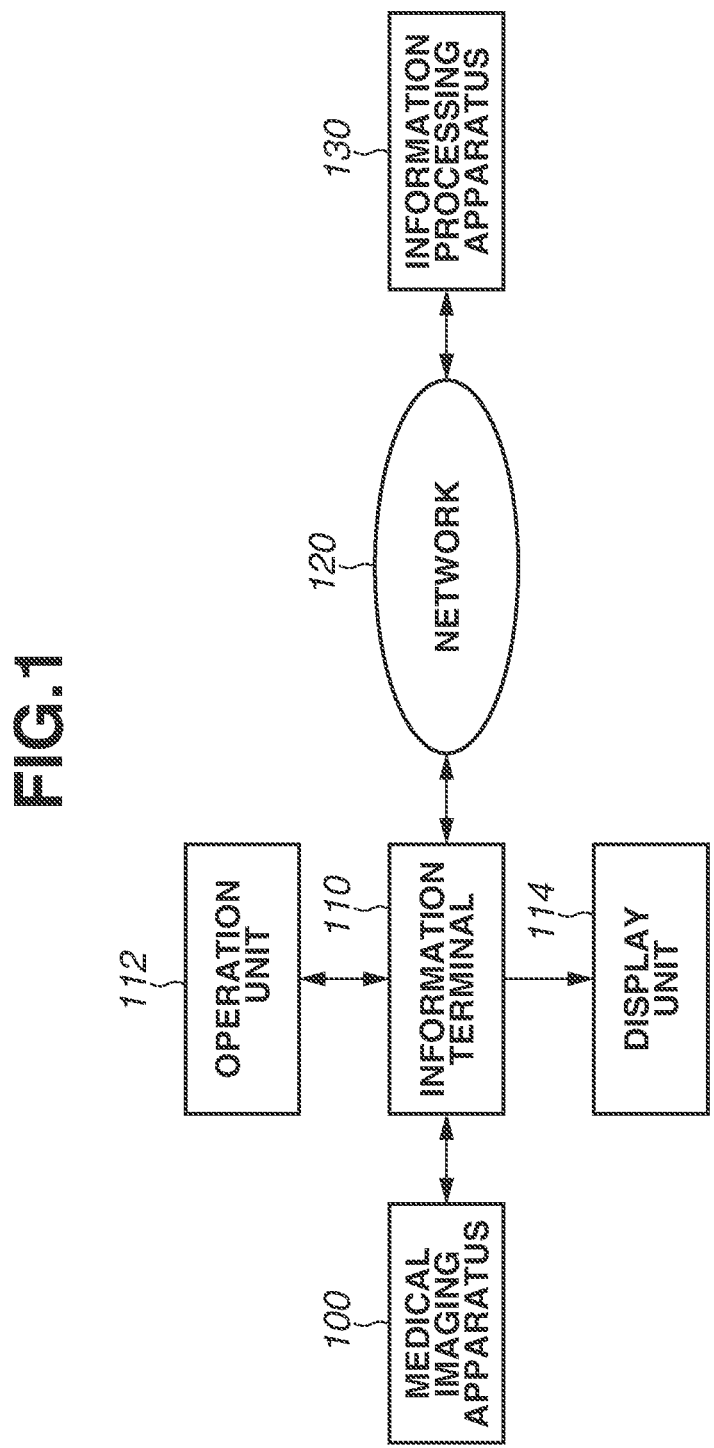
FIG. 1 is a block diagram illustrating a configuration of an information processing system according to a first exemplary embodiment of the present disclosure.

FIG. 1 illustrates a configuration of an information processing system according to a first exemplary embodiment of the present disclosure.

The information processing system according to the present exemplary embodiment includes a medical imaging apparatus 100 that acquires medical data about a subject, an information terminal 110, a network 120, and an information processing apparatus 130. The information terminal 110 may be one or more information terminals.

The information terminal 110 is connected to each of an operation unit 112 and a display unit 114. The operation unit 112 receives various instructions from an operator, and transmits various instructions to each of the information terminal 110 and the medical imaging apparatus 100. Examples of the operation unit 112 include a mouse, a keyboard, a button, a panel switch, a foot switch, a trackball, and a joystick. The display unit 114 displays a graphical user interface (GUI) for inputting various instructions on the operation unit 112, and displays image data based on the medical data acquired by the medical imaging apparatus 100.

In the configuration illustrated in FIG. 1, the operation unit 112 and the display unit 114 are provided separately from the information terminal 110. However, the information terminal 110 may internally have the functions of the operation unit 112 and the display unit 114.

The medical imaging apparatus 100 acquires medical data about a subject. Examples of the medical imaging apparatus 100 include an X-ray computed tomography (CT) apparatus, a magnetic resonance imaging (MRI) apparatus, and an ultrasonic diagnosis apparatus.

The X-ray CT apparatus includes an X-ray source and an X-ray detector. The X-ray CT apparatus generates CT data by irradiating a subject with an X-ray from the X-ray source and reconstructing data detected by the X-ray detector while rotating the X-ray source and the X-ray detector around the subject.

The MRI apparatus generates a predetermined magnetic field on a subject placed in a static magnetic field, and performs a Fourier transform on acquired data to generate MRI data.

The ultrasonic diagnosis apparatus transmits an ultrasonic wave to a subject, receives an ultrasonic wave as a reflected wave from the subject, and generates ultrasonic wave data.

The medical data (such as CT data, MRI data, or ultrasonic data) generated by the medical imaging apparatus 100 is three-dimensional data (volume data) or two-dimensional data. The medical data is, for example, image data about the subject. The image data includes raw data. The medical image data may be moving image data containing a plurality of pieces of frame data. The medical data also includes measurement data obtained by various measurements using the medical image data.

The medical imaging apparatus 100 is connected to the information terminal 110. Examples of the information terminal 110 include a personal computer (PC) terminal, a mobile phone such as a smartphone, a notebook terminal, and a tablet terminal. The information terminal 110 can set subject information and can associate the subject information with the medical data acquired from the medical imaging apparatus 100. The information terminal 110 can also display various data such as medical data and measurement data acquired from the medical imaging apparatus 100.

The information terminal 110 and the information processing apparatus 130 are each connected to the network 120. The network 120 includes communication networks outside a hospital, such as a wireless communication (Wi-Fi®), the Internet, a wireless base station, a provider, and a communication line. The network 120 may also include an intranet as a communication network in the hospital. The information terminal 110 can communicate with the information processing apparatus 130 via the network 120. The information terminal 110 can transmit medical data (including medical image data), information about inference, model selection information, and the like to the information processing apparatus 130. The information processing apparatus 130 can transmit, to the information terminal 110, inference results obtained by inference processing using the medical data (including the medical image data).

Figure 2:
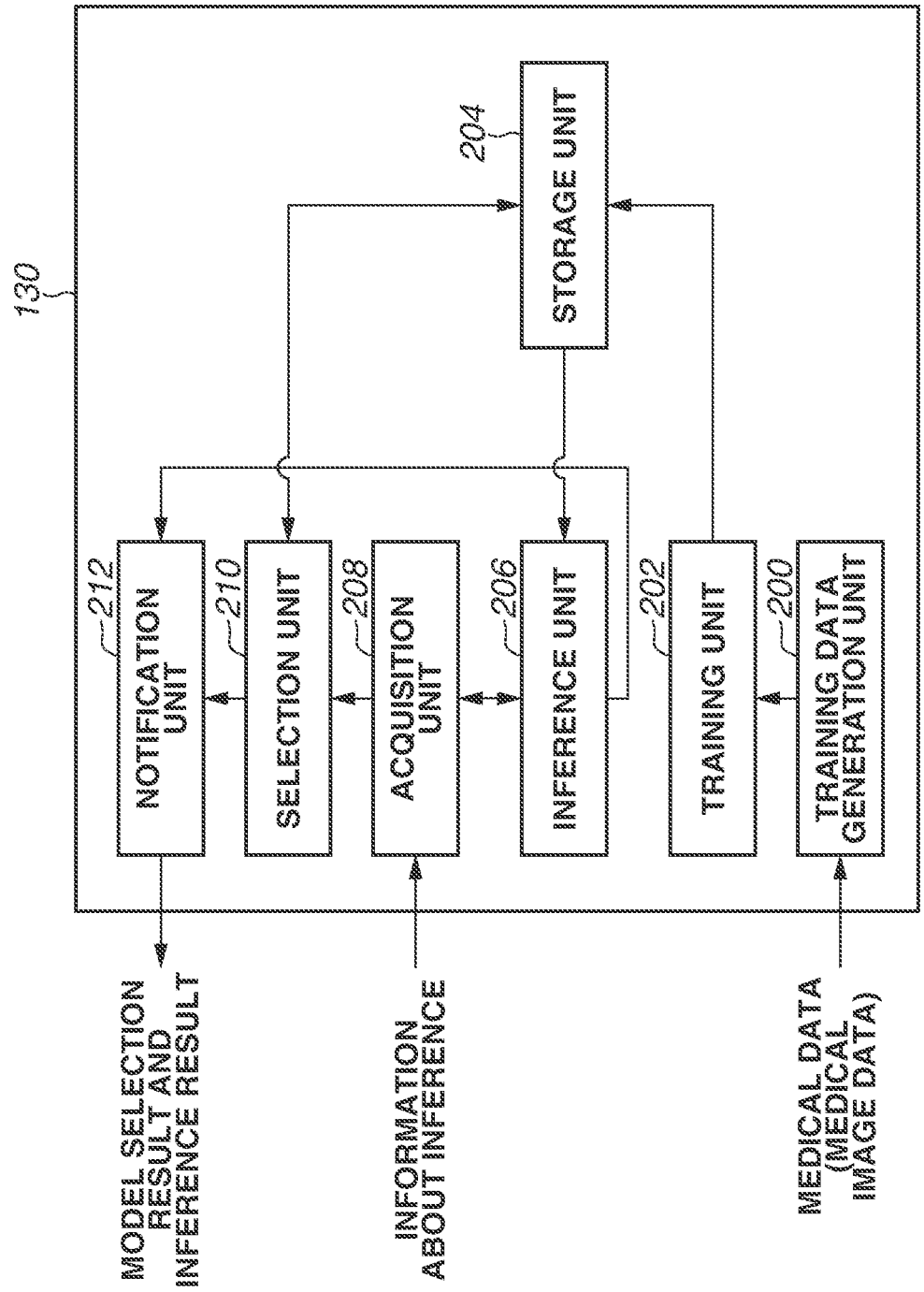
FIG. 2 is a block diagram illustrating a configuration of an information processing apparatus according to the first exemplary embodiment.

FIG. 2 illustrates a configuration of the information processing apparatus 130 according to the present exemplary embodiment. The information processing apparatus 130 includes a training data generation unit 200 that generates training data using medical image data, and a training unit 202 that performs training about medical image data using the training data generated by the training data generation unit 200. The information processing apparatus 130 further includes a storage unit 204 that stores trained models generated by the training unit 202 in association with class hierarchies, and an inference unit 206 that performs inference using the trained models. The information processing apparatus 130 further includes an acquisition unit 208, a selection unit 210, and a notification unit 212. The acquisition unit 208 acquires information about inference. The selection unit 210 selects a plurality of trained models having a hierarchical relationship, based on the information about inference acquired by the acquisition unit 208. The notification unit 212 provides a notification of the plurality of trained models selected by the selection unit 210.

The components (functions) of the information processing apparatus 130 are implemented for example by a processor, such as a central processing unit (CPU) or a graphics processing unit (GPU), executing programs (software) stored in a memory.

The information processing apparatus 130 includes therein the processor and the memory. The processor can perform each processing of the information processing apparatus 130 based on the programs stored in the memory, and can be caused to function as the training data generation unit 200, the training unit 202, the storage unit 204, the inference unit 206, the acquisition unit 208, the selection unit 210, the notification unit 212, and the like.

The information about inference acquired by the acquisition unit 208 is at least one of, for example, inference target medical image data, information indicating an inference purpose, and information indicating a class.

The training data generation unit 200 is connected to the network 120, and can acquire medical data including medical image data and measurement data. The training data generation unit 200 generates training data using medical image data. The training data generated by the training data generation unit 200 is determined depending on the target of the inference task or classification to be performed by a neural network.

Examples of the inference task to be performed by the neural network include a classification task for classifying medical image data into classes, a detection task for detecting what object is captured in the medical image data and the location of the object, and a segmentation task for extracting a target region from the medical image data.

In the case of training a neural network for performing the classification task, the training data generation unit 200 generates, as training data, a pair of medical image data and a correct answer label that is a label indicating the object captured in the medical image data.

In a case where the detection task is to be performed by a neural network, the training data generation unit 200 generates, as training data, a pair of medical image data and a correct answer image obtained by adding a region of interest (ROI), which indicates the location of the object captured in the medical image data, and a correct answer label, which is a label indicating the object, to the medical image data.

In a case where the segmentation task is to be performed by a neural network, the training data generation unit 200 generates, as training data, a pair of medical image data and a correct answer image obtained by adding pixel position information about the object captured in the medical image data and a correct answer label, which is a label indicating the object, to the medical image data.

For example, in a case where the neural network for performing the segmentation task on the presence or absence of pathology and the type and region of pathology is caused to perform training using the medical image data acquired from the information terminal 110, the training data generation unit 200 generates, as training data, a pair of medical image data including a pathology region, and a correct answer image obtained by adding information about a correct answer label indicating the type of pathology and pixel position information about the pathology to the medical image data.

Furthermore, the training data generation unit 200 may perform preprocessing on the medical data depending on the neural network that is to perform training in the training unit 202. For example, if the target of inference by the neural network is medical image data, the training data generation unit 200 performs processing, such as noise reduction, filter processing, image clipping, or resolution change, on the acquired medical image data. If the target of inference by the neural network is a natural language such as text, the training data generation unit 200 performs preprocessing, such as performing morphological analysis and applying a vector transformation technique, on processing target data depending on the inference target of the neural network and the task.

While FIG. 2 illustrates the configuration in which the training data generation unit 200 is included in the information processing apparatus 130, the information terminal 110 may include the training data generation unit 200. In other words, the training data generation unit 200 may be held as a component of the information terminal 110. For example, training processing using the neural network may be performed by the training unit 202 of the information processing apparatus 130 via the network 120 after the above-described training data is generated in the information terminal 110.

The training unit 202 is connected to the training data generation unit 200. The training unit 202 generates a trained model by using the neural network to learn the medical image data in association with the training data. In this case, the trained model indicates a parameter determined by performing training processing until a predetermined criterion is satisfied, and information about a model corresponding to the parameter. The trained model may be used in training for another model as transfer training, or training processing may be further performed on the trained model.

Neural networks generally include a plurality of layers. Among the neural networks, in particular, a convolutional neural network (CNN), which is a type of a deep training technique, includes a plurality of intermediate layers (not illustrated) between an input layer and an output layer. The plurality of intermediate layers includes a convolution layer, a pooling layer, an upsampling layer, and a combination layer. The convolution layer performs convolution processing on a group of input values. In the convolution layer, the input medical image data is convolved to extract features from the medical image data.

The pooling layer performs processing for making the number of groups of output values smaller than that of groups of input values by reducing or combining the groups of input values. The upsampling layer performs processing for making the number of groups of output values larger than that of groups of input values by duplicating the groups of input values or adding values interpolated from the groups of input values. The combination layer performs processing for inputting groups of values, such as a group of output values of a certain layer and a group of pixel values constituting the medical image data, from a plurality of sources, and combining the groups of values by connecting or adding the groups of values. The number of intermediate layers can be changed as needed based on the training contents.

The storage unit 204 is connected to the training unit 202. The storage unit 204 stores a plurality of class hierarchies and trained models respectively corresponding to the plurality of class hierarchies. Each class hierarchy corresponds to a class into which a trained model classifies medical image data. For example, a first class hierarchy corresponds to a class in which an organ region is classified, and a second class hierarchy corresponds to a class in which an abnormality is detected from a specific region. The storage unit 204 stores trained models for classifying medical image data into classes respectively belonging to the class hierarchies, in association with the class hierarchies. For example, a trained model that corresponds to the first class hierarchy and can specify a lung field region, and a trained model that corresponds to the second class hierarchy and can detect an abnormal region from the lung field region are defined to have a hierarchical relationship. The hierarchical relationship indicates the flow of inference using trained models. For example, the following flow is stored as the hierarchical relationship in the storage unit 204. When a CT image is input, a first trained model for inferring a lung field region from the CT image is applied, and a second trained model infers an abnormal region from the inferred lung field region.

Each trained model stored in the storage unit 204 has been trained, for example, to detect or extract an organ region or a pathology region from medical image data. In this case, each trained model is generated using, for example, a neural network. However, each trained model may be generated using not only the CNN, which is one of the deep training techniques among the neural network techniques, a recurrent neural network (RNN), and models derived from the CNN or RNN, but also other machine training techniques such as a support vector machine, logistic regression, and random forest, or rule-based methods.

The inference unit 206 can acquire medical data including medical image data and measurement data from the acquisition unit 208. The inference unit 206 is connected to the storage unit 204, and can perform inference processing using a trained model selected by the selection unit 210 (described below) from among the trained models stored in the storage unit 204. For example, the inference unit 206 performs inference processing on newly generated medical image data by using a trained model that has been trained to extract the type and region of pathology from medical image data. If the pathology is included in the newly generated medical image data, the inference unit 206 can output the type and region of the pathology. If a plurality of trained models having a hierarchical relationship is selected by the selection unit 210, the inference unit 206 performs inference processing using a trained model corresponding to a higher class hierarchy, among the plurality of trained models having the hierarchical relationship, and with an input based on the result of the inference processing, further performs inference processing using a trained model corresponding to a lower class hierarchy. In other words, the inference unit 206 performs inference processing using a plurality of selected trained models having a hierarchical relationship.

Figure 3:
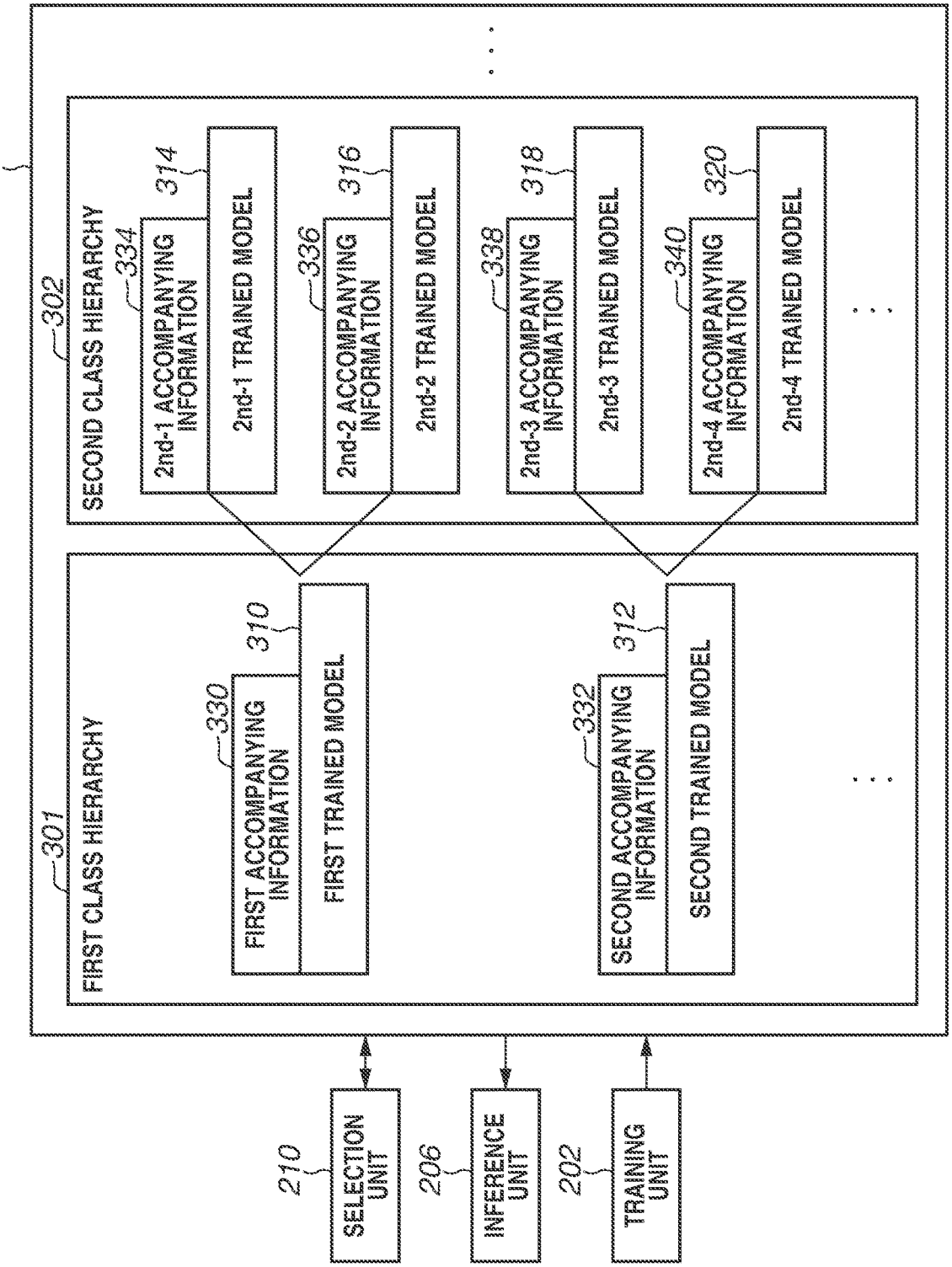
FIG. 3 is a block diagram illustrating a storage unit in the information processing apparatus according to the first exemplary embodiment.

FIG. 3 illustrates a configuration of the storage unit 204 according to the present exemplary embodiment. The storage unit 204 stores a plurality of trained models, which has been trained by the training unit 202, and accompanying information thereof in association with class hierarchies. Each class hierarchy corresponds to a class in which a trained model performs inference, and the trained model for classifying medical image data into the class belonging to the class hierarchy is stored in association with the class hierarchy. A higher class corresponds to a class hierarchy in which inferred processing is to be performed at an earlier stage on the medical image data acquired by the medical imaging apparatus 100, and a lower class corresponds to a class hierarchy in which inference processing is to be performed at a later stage on the medical image data. The inference unit 206 performs inference processing using the trained model corresponding to the higher class hierarchy, thereby improving the inference performance of the trained model corresponding to the lower class hierarchy. As functions for assisting the trained model corresponding to the lower class hierarchy, for example, organ region extraction and noise reduction are performed in the inference processing using the trained model corresponding to the higher class hierarchy. In the example of FIG. 3, the storage unit 204 is formed of, for example, a first class hierarchy 301 and a second (2nd) class hierarchy 302. For example, the first class hierarchy 301 corresponds to a class in which an organ region is inferred, and the second class hierarchy 302 corresponds to a class in which an abnormality region is inferred from a specific region. The storage unit 204 may be formed of three or more class hierarchies. Each of the plurality of class hierarchies stored in the storage unit 204 stores a plurality of trained models for performing inference processing in the class corresponding to the class hierarchy.

In the first class hierarchy 301 in the storage unit 204, a first trained model 310 and first accompanying information 330 added to the first trained model 310 are stored. Furthermore, in the first class hierarchy 301 in the storage unit 204, a second trained model 312 and second accompanying information 332 added to the second trained model 312 are stored.

In the second class hierarchy 302 in the storage unit 204, a 2nd-1 trained model 314 and 2nd-1 accompanying information 334 added thereto, a 2nd-2 trained model 316 and 2nd-2 accompanying information 336 added thereto, a 2nd-3 trained model 318 and 2nd-3 accompanying information 338 added thereto, and a 2nd-4 trained model 320 and 2nd-4 accompanying information 340 added thereto are stored.

In this example, the first trained model 310 in the first class hierarchy 301 has a hierarchical relationship with the 2nd-1 trained model 314 and the 2nd-2 trained model 316 in the second class hierarchy 302. The hierarchical relationship is schematically represented by lines in FIG. 3. Furthermore, the second trained model 312 in the first class hierarchy 301 has a hierarchical relationship with the 2nd-3 trained model 318 and the 2nd-4 trained model 320 in the second class hierarchy 302. The hierarchical relationship corresponds to the flow of a plurality of inferences to be performed on, for example, medical image data. For example, for the flow of obtaining an output by performing a first inference and then a second inference based on the first inference result, the storage unit 204 stores a trained model for performing the first inference and a trained model for performing the second inference, as trained models having a hierarchical relationship. For ease of explanation, the hierarchical relationship is represented by the lines in FIG. 3. However, for example, the accompanying information that accompanies each trained model stores information indicating a trained model for performing the second inference to be performed after the first inference, as the hierarchical relationship. Also, in cases other than the case where the accompanying information that accompanies a trained model corresponding to a higher class hierarchy stores information indicating a trained model corresponding to a lower class hierarchy, the accompanying information that accompanies the trained model corresponding to the lower class hierarchy may store information indicating the trained model corresponding to the higher class hierarchy. Furthermore, the accompanying information that accompanies the trained model corresponding to the higher class hierarchy and the accompanying information that accompanies the trained model corresponding to the lower class hierarchy may store information indicating the trained model corresponding to the lower class hierarchy and information indicating the trained model corresponding to the higher class hierarchy, respectively.

The storage unit 204 stores a plurality of trained models in association with a plurality of respective class hierarchies, and stores a hierarchical relationship between the plurality of trained models. This configuration enables the selection unit 210 (described below) to select trained models having a hierarchical relationship, thereby saving time and effort for a user to select models and to perform output and input processing on the plurality of selected models. While FIG. 3 illustrates the configuration in which six trained models are stored together with the accompanying information in the storage unit 204, the storage unit 204 can also store seven or more trained models together with the accompanying information. It is assumed here that at least one of an inference task, a class indicating a classification target, a model structure, and training data is different among the plurality of trained models. Furthermore, each trained model can be designated or specified based on the accompanying information added to the trained model. Furthermore, trained models having a hierarchical relationship can be designated and specified based on the accompanying information.

The inference unit 206 performs inference processing on inference target data acquired from the information terminal 110 by using an appropriate trained model selected based on accompanying information by the selection unit 210 in response to an input from the information terminal 110.

The inference unit 206 performs inference processing on inference target medical image data by using, for example, a trained model that has been trained to extract a pathology region or an organ region from medical image data. In a case where a plurality of trained models having a hierarchical relationship is selected by the selection unit 210, the inference unit 206 performs inference using a trained model corresponding to a higher class hierarchy and, with an input based on the result of the inference, further performs inference using a trained model corresponding to a lower class hierarchy. The inference unit 206 performs inference processing using the trained model corresponding to the higher class hierarchy and further performs inference processing using the trained model corresponding to the lower class hierarchy having a hierarchical relationship with the trained model corresponding to the higher class hierarchy, thereby improving the accuracy of the inference processing result to be output.

The inference unit 206 may cause the notification unit 212 to provide a notification of respective inference results from the plurality of trained models that is selected by the selection unit 210 and has a hierarchical relationship, or may cause the notification unit 212 to provide a notification of the inference result from the trained model corresponding to the lowest class.

The acquisition unit 208 acquires information about inference from the information terminal 110. The information about inference includes, for example, at least one of inference target medical image data, information indicating an inference purpose, and information indicating a class. For example, when the user operates the information terminal 110 to transmit the inference target medical image data, the acquisition unit 208 acquires the transmitted information about inference and transmits the acquired information to the selection unit 210. If the acquired information about inference is insufficient, the acquisition unit 208 causes the notification unit 212 to provide a notification prompting the user to transmit additional information. Furthermore, the acquisition unit 208 may acquire trained model selection information. The selection unit 210 selects a trained model based on the acquired selection information, and the inference unit 206 performs inference processing using the selected trained model. The selection information is input by the user through, for example, the operation unit 112 of the information terminal 110.

Based on the information about inference acquired by the acquisition unit 208, the selection unit 210 selects a plurality of trained models having a hierarchical relationship from among those stored in the storage unit 204, as trained models for use in inference processing by the inference unit 206.

For example, in a case where medical image data is acquired as the information about inference by the acquisition unit 208, the selection unit 210 calculates a degree of conformity with a trained model corresponding to each of the plurality of class hierarchies, and selects a plurality of trained models having a hierarchical relationship based on the degree of conformity. The degree of conformity may be calculated by, for example, using a trained model to obtain a probability that the object corresponding to the class belonging to the class hierarchy may be present in the target medical image data. Alternatively, the degree of conformity may be detected by other detection methods. Further alternatively, the degree of conformity may be calculated, for example, based on the degree of similarity with training data for a trained model corresponding to each class hierarchy. The selection unit 210 calculates the degree of conformity and selects trained models from among the trained models corresponding to the class hierarchies with the calculated degree of conformity being greater than a predetermined value. The selection unit 210 selects a trained model corresponding to a lowest class hierarchy from among the trained models with the degree of conformity being greater than the predetermined value, and selects a trained model that has a hierarchical relationship with the trained model corresponding to the lowest class hierarchy and corresponds to a higher class hierarchy, based on the accompanying information that accompanies the selected trained model. If there are three or more class hierarchies, three or more trained models are selected depending on the hierarchical relationship. The selection method used by the selection unit 210 is not limited to the above-described method. A plurality of trained models having a hierarchical relationship may be selected so that the plurality of trained models includes a trained model with the highest degree of conformity.

Furthermore, the selection unit 210 may select the trained model corresponding to the highest class hierarchy from among the trained models with the degree of conformity being greater than the predetermined value. The selection unit 210 selects a trained model corresponding to a lower class hierarchy based on the accompanying information that accompanies the selected trained model corresponding to the highest class hierarchy. In a case where there are three or more class hierarchies, three or more trained models are selected depending on the hierarchical relationship.

In a case where the information about inference acquired by the acquisition unit 208 indicates an inference purpose or a class, the selection unit 210 calculates the degree of conformity between information about the inference purpose or the class and the class hierarchies in the storage unit 204. The degree of conformity is, for example, the degree of similarity between a vector for the information about the inference purpose or the class and a vector for a class constituting a class hierarchy. Alternatively, the likelihood obtained by inference processing performed by a trained model using the vector for the information about the inference purpose or the class as an input may be used as the degree of conformity.

In a case where the information acquired by the acquisition unit 208 is the information about the inference purpose or the class, and medical image data, the selection unit 210 first calculates the degree of conformity based on the information about the inference purpose or the class using the above-described method. Next, the selection unit 210 calculates the degree of conformity based on the medical image data using the above-described method. Lastly, the selection unit 210 selects a plurality of trained models having a hierarchical relationship based on both the degrees of conformity using the above-described method. The selection unit 210 may select trained models by comparing each of the degrees of conformity with a predetermined value, or may select trained models by comparing the degree of conformity calculated by combination (addition or multiplication) of the both degrees of conformity, with a predetermined value. When a plurality of trained models having a hierarchical relationship is selected by the selection unit 210, information about the selected trained models is transmitted to the notification unit 212.

If the acquisition unit 208 acquires model selection information input by the user, for example, from the information terminal 110 after or before the notification by the notification unit 212, the selection unit 210 selects a plurality of trained models having a hierarchical relationship based on the selection information.

The notification unit 212 provides a notification of information about the trained models selected by the selection unit 210. The notification by the notification unit 212 is provided to the information terminal 110 that is connectable to the information processing apparatus 130 via the network 120. The notification unit 212 also provides a notification of the inference result by the inference unit 206 to the information terminal 110.

In sum, the information processing apparatus 130 according to the present exemplary embodiment includes the storage unit 204, the acquisition unit 208, the selection unit 210, and the notification unit 212. The storage unit 204 stores a plurality of trained models including a first trained model for classifying medical image data into a class belonging to a first class hierarchy, and a second trained model for classifying the medical image data into a class belonging to a second class hierarchy lower than the first class hierarchy. The acquisition unit 208 acquires information about inference. The selection unit 210 selects a plurality of trained models having a hierarchical relationship, based on the information about inference acquired by the acquisition unit 208. The notification unit 212 provides a notification of the plurality of trained models selected by the selection unit 210. This configuration makes it possible to select a plurality of trained models having a hierarchical relationship from among a plurality of trained models, thereby saving time and effort for the user to select trained models from among the plurality of trained models and to perform output and input processing on the plurality of selected trained models.

Figure 4:
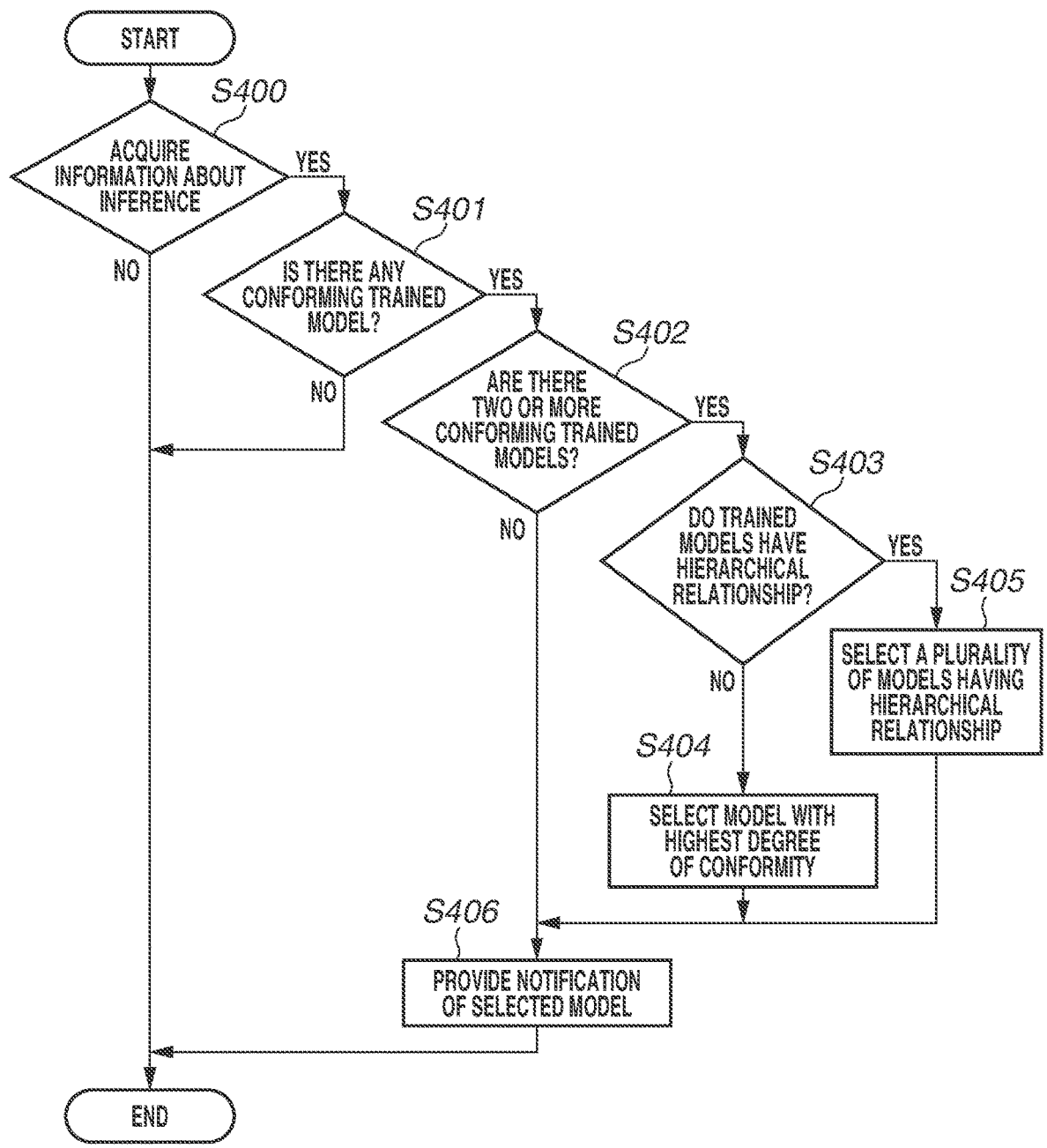
FIG. 4 is a flowchart illustrating trained model selection processing according to the first exemplary embodiment.

Processing performed when the selection unit 210 selects trained models for performing inference processing, based on information about inference will be described next with reference to FIG. 4.

In step S400, the acquisition unit 208 acquires information about inference. If the information about inference is acquired by the acquisition unit 208 (YES in step S400), the processing proceeds to step S401. If the information about inference is not acquired (NO in step S400), the processing ends.

In step S401, the selection unit 210 calculates the degree of conformity with each class hierarchy using any one of the above-described methods, and determines whether the calculated degree of conformity is greater than a predetermined value. If the degree of conformity calculated by the selection unit 210 is greater than the predetermined value (YES in step S401), the processing proceeds to step S402. If the degree of conformity calculated by the selection unit 210 is less than or equal to the predetermined value (NO in step S401), the processing ends.

In step S402, the selection unit 210 determines whether two or more trained models are determined to have a greater degree of conformity than the predetermined value. If the selection unit 210 determines that two or more trained models are determined to have a greater degree of conformity than the predetermined value (YES in step S402), the processing proceeds to step S403. If the selection unit 210 determines that one trained model is determined to have a greater degree of conformity than the predetermined value (NO in step S402), the processing proceeds to step S406.

In step S403, the selection unit 210 determines whether the plurality of trained models has a hierarchical relationship. The determination by the selection unit 210 is made by referring to the accompanying information that accompanies each of the two or more trained models. If the selection unit 210 determines that there are no trained models having a hierarchical relationship (NO in step S403), the processing proceeds to step S404. If there are trained models having a hierarchical relationship (YES in step S403), the processing proceeds to step S405.

In step S404, the selection unit 210 selects a trained model having the highest degree of conformity from among the plurality of trained models, as the trained model for use in inference processing by the inference unit 206.

In step S405, the plurality of trained models having a hierarchical relationship is selected as the trained models for use in inference processing by the inference unit 206.

In step S406, the notification unit 212 provides a notification of the trained model(s) selected by the selection unit 210.

Figure 5:
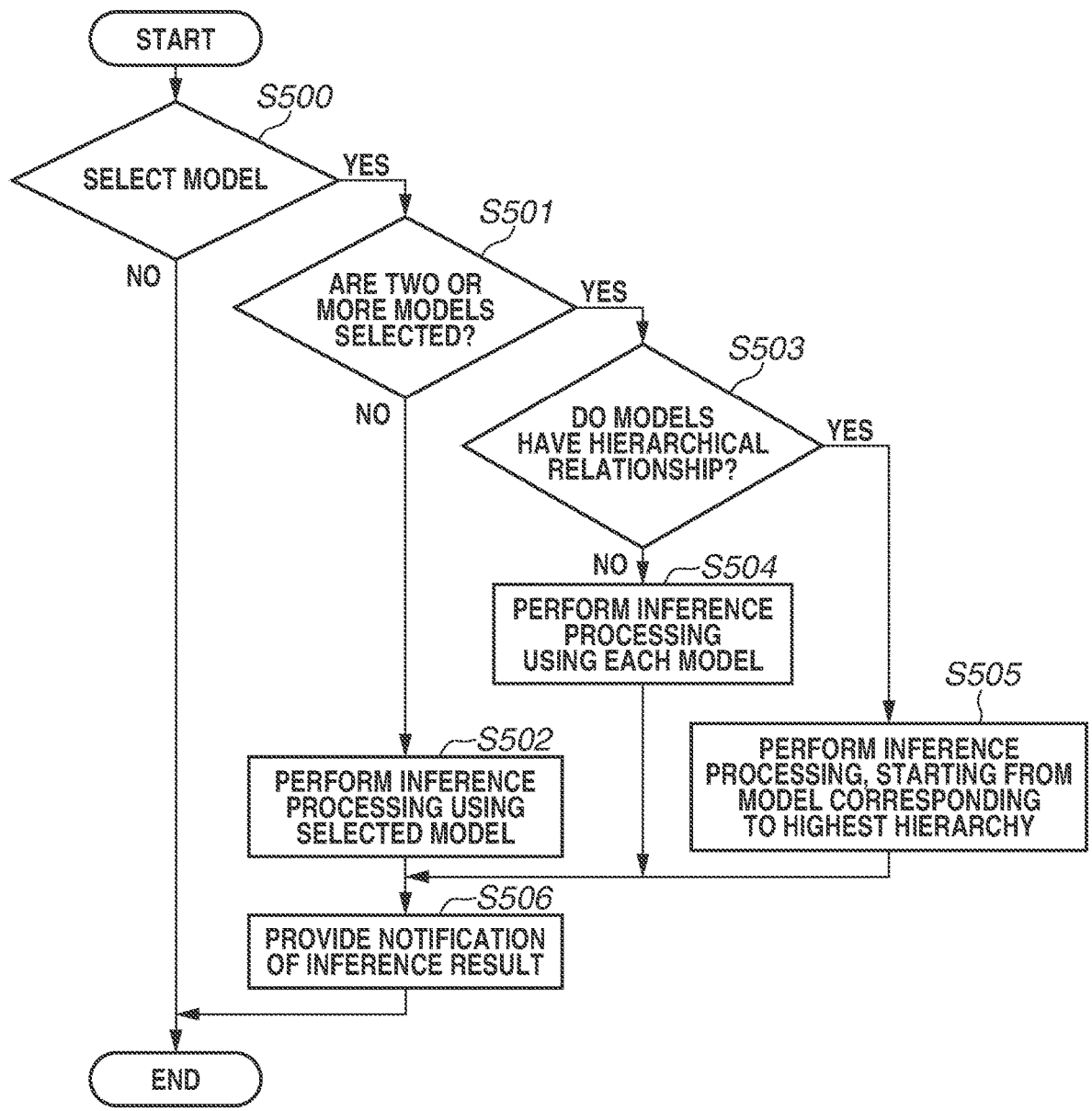
FIG. 5 is a flowchart illustrating inference processing using a trained model according to the first exemplary embodiment.

Next, processing performed when the inference unit 206 performs inference processing using a trained model selected by the selection unit 210 will be described with reference to FIG. 5.

In step S500, if a trained model is selected by the selection unit 210 (YES in step S500), the processing proceeds to step S501. If no trained model is selected (NO in step S500), the processing ends.

In step S501, the inference unit 206 determines whether two or more trained models are selected by the selection unit 210. If one trained model is selected (NO in step S501), the processing proceeds to step S502. If two or more trained models are selected (YES in step S501), the processing proceeds to step S503.

In step S502, the inference unit 206 performs inference processing on medical image data by using the trained model selected by the selection unit 210. After the inference processing using the selected trained model, the inference unit 206 transmits the inference result to the notification unit 212, and then the processing proceeds to step S506.

In step S503, the inference unit 206 determines whether the two or more trained models have a hierarchical relationship. If the two or more trained models do not have a hierarchical relationship (NO in step S503), the processing proceeds to step S504. If the two or more trained models have a hierarchical relationship (YES in step S503), the processing proceeds to step S505.

In step S504, the inference unit 206 performs inference processing using each of the two or more trained models that do not have a hierarchical relationship. After the inference processing using the trained models, the inference unit 206 transmits the inference results to the notification unit 212, and then the processing proceeds to step S506.

In step S505, the inference unit 206 performs inference processing, starting from the trained model corresponding to the highest class hierarchy among the plurality of trained models having the hierarchical relationship. A case where the first trained model 310 corresponding to the first class hierarchy 301 and the 2nd-1 trained model 314 corresponding to the second class hierarchy 302 are selected will be described now. The inference unit 206 applies the first trained model 310 to the medical image data to perform inference processing and acquire a first inference result. Next, the inference unit 206 gives an input based on the first inference result from the first trained model 310 to the 2nd-1 trained model 314, and further performs inference processing to acquire a second inference result. After the inference processing using the trained models, the inference unit 206 transmits the inference result to the notification unit 212, and then the processing proceeds to step S506.

In step S506, the notification unit 212 provides a notification of the inference result obtained using the trained model(s) selected by the selection unit 210. The notification by the notification unit 212 is provided to, for example, the information terminal 110 that can communicate with the information processing apparatus 130 via the network 120. The method for the provision of the notification by the notification unit 212 is not particularly limited as long as the notification can be provided to the user that wishes to perform inference. For example, the user may check the notification provided by the notification unit 212 by accessing the information processing apparatus 130 or a display unit (not illustrated) included in the information processing apparatus 130.

The information processing apparatus 130 according to the present exemplary embodiment can select a plurality of trained models having a hierarchical relationship from among a plurality of trained models, and can perform inference processing using the plurality of selected trained models having the hierarchical relationship. A modified example of the present exemplary embodiment will be described.

In the above-described exemplary embodiment, the selection unit 210 calculates the degree of conformity between information about inference and each class hierarchy, and selects trained models for use in inference processing by the inference unit 206, from among the trained models with the degree of conformity being greater than the predetermined value.

In the present modified example, if the trained model corresponding to the lowest or highest class hierarchy in the plurality of trained models that is selected by the selection unit 210 and has a hierarchical relationship further has a hierarchical relationship with a trained model corresponding to a higher or lower class hierarchy, the selection unit 210 may further select the trained model as a recommended trained model, and the notification unit 212 may provide a notification for recommending the selection of the trained model.

In the above-described exemplary embodiment, the selection unit 210 calculates the degree of conformity between information about inference and a class corresponding to a class hierarchy, and selects the trained model corresponding to the lowest or highest class hierarchy from among the trained models with the degree of conformity being greater than the predetermined value. In a second exemplary embodiment, if the storage unit 204 stores the trained model corresponding to the highest class hierarchy and the trained model corresponding the lowest class hierarchy among the trained models with the degree of conformity being greater than the predetermined value, and also stores another class hierarchy between the lowest class hierarchy and the highest class hierarchy, the selection unit 210 further selects a trained model from the other class hierarchy between the lowest class hierarchy and the highest class hierarchy. The present exemplary embodiment will be described with reference to FIG. 6.

The storage unit 204 further includes an Nth class hierarchy 603. N is a natural number that is greater than or equal to 3, and is set depending on the number of class hierarchies.

For ease of explanation, it is assumed here that N is 3. In the present exemplary embodiment, the selection unit 210 selects the trained model corresponding to the highest class hierarchy from among the trained models with the degree of conformity being greater than the predetermined value, and further selects the trained model corresponding to the lowest class hierarchy. If the trained models selected by the selection unit 210 have a hierarchical relationship (if the trained models can be searched based on the accompanying information that accompanies at least one of the trained models) and if there is another class hierarchy between the class hierarchies corresponding to the selected trained models, the selection unit 210 further selects a trained model having a hierarchical relationship with the selected trained models, from among the trained models corresponding to the other class hierarchy between the highest class hierarchy and the lowest class hierarchy, as the trained model for use in inference processing by the inference unit 206. For example, a case will be described where the selection unit 210 selects the first trained model 310 as the trained model corresponding to the highest class hierarchy and selects an Nth-1 trained model 614 as the trained model corresponding to the lowest class hierarchy from among the trained models with the degree of conformity being greater than the predetermined value. The selection unit 210 determines whether the first trained model 310 and the Nth-1 trained model 614 have a hierarchical relationship. If the selection unit 210 determines that the first trained model 310 and the Nth-1 trained model 614 have a hierarchical relationship, the selection unit 210 further determines whether there is another class hierarchy between the Nth class hierarchy 603 corresponding to the Nth-1 trained model 614 and the first class hierarchy 301 corresponding to the first trained model 310. If there is another class hierarchy between the first class hierarchy 301 and the Nth class hierarchy 603, the selection unit 210 further selects a trained model having a hierarchical relationship with the first trained model 310 and the Nth-1 trained model 614 from among the trained models corresponding to the other class hierarchy between the first class hierarchy 301 and the Nth class hierarchy 603.

A flow of processing according to the present exemplary embodiment will be described with reference to FIG. 7. In step S700, the selection unit 210 determines whether there is any other class hierarchy between the highest class hierarchy and the lowest class hierarchy corresponding to the trained models that have a hierarchical relationship and have the calculated degree of conformity that is greater than the predetermined value. If the selection unit 210 determines that there is no other class hierarchy (NO in step S700), the processing returns to the above-described step S405. If the selection unit 210 determines that there is any other hierarchy (YES in step S700), the processing proceeds to step S702.

In step S702, the selection unit 210 further selects a trained model that has a hierarchical relationship with the trained model corresponding to the highest class hierarchy and the trained model corresponding to the lowest class hierarchy (i.e., a trained model that can be searched based on the accompanying information) from among the trained models corresponding to the other hierarchy. Not only trained models having a direct hierarchical relationship, such as the first trained model 310 and the 2nd-1 trained model 314, but also trained models that can be searched based on the accompanying information that accompanies one of the trained models, such as the first trained model 310 and the Nth-1 trained model 614, are defined to have a hierarchical relationship.

The information processing apparatus 130 according to the present exemplary embodiment can specify a range in which the selection unit 210 selects appropriate trained models from among a plurality of trained models, thereby saving time and effort for the user to select trained models from among a plurality of trained models and to perform output and input processing on the plurality of selected trained models.

While in the above-described exemplary embodiments, the configuration in which a plurality of trained models having a hierarchical relationship is selected by the selection unit 210 has been described, in a third exemplary embodiment, a configuration in which a plurality of trained models having a hierarchical relationship is selected a plurality of times by the selection unit 210.

Referring to FIG. 3, a case where the selection unit 210 selects, for example, the first trained model 310 and the 2nd-1 trained model 314 having a hierarchical relationship with the first trained model 310 as a first candidate, and selects the second trained model 312 and the 2nd-3 trained model 318 having a hierarchical relationship with the second trained model 312 as a second candidate will be described. If a plurality of candidates is selected by the selection unit 210, the selection unit 210 further compares the degrees of conformity of the plurality of candidates. In the comparison of the degrees of conformity by the selection unit 210, for example, the candidate including the trained model for classifying the class with the highest degree of conformity is selected as the trained models for use in inference processing by the inference unit 206. Alternatively, for example, the candidate with a larger total value of the degrees of conformity of the trained models in the candidates can be selected. If there is only a small difference between the degrees of conformity between the plurality of candidates selected by the selection unit 210, the notification unit 212 provides a notification for recommending the selection of any one of the candidates.

According to the present exemplary embodiment, also when a plurality of trained models having a plurality of hierarchical relationships is selected as candidates for use in inference processing on medical image data, a plurality of trained models having an appropriate hierarchical relationship can be selected.

In a fourth exemplary embodiment, a configuration in which trained models are selected by the selection unit 210 in a case where the trained model corresponding to the lowest class hierarchy selected from among trained models with the degree of conformity being greater than the predetermined value has a hierarchical relationship with a plurality of trained models.

Referring to FIG. 8, the storage unit 204 according to the present exemplary embodiment includes a first class hierarchy 801 and a second class hierarchy 802. The first class hierarchy 801 stores a first trained model 810, first accompanying information 830 that accompanies the first trained model 810, a second trained model 812, and second accompanying information 832 that accompanies the second trained model 812. The second class hierarchy 802 stores a 2nd-2 trained model 816 having a hierarchical relationship with each of the first trained model 810 and the second trained model 812, and 2nd-2 accompanying information 836 that accompanies the 2nd-2 trained model 816.

It is assumed here that in the selection processing by the selection unit 210, the first trained model 810 and the 2nd-2 trained model 816 are selected as the first candidate for the trained models that have a hierarchical relationship and have the calculated degree of conformity that is greater than the predetermined value, and the second trained model 812 and the 2nd-2 trained model 816 are selected as the second candidate.

If a plurality of candidates is selected, appropriate trained models are selected by comparing the total values of the degrees of conformity of the plurality of candidates. Furthermore, if three or more class hierarchies, such as the class hierarchies described above with reference to FIG. 6, are stored in the storage unit 204 and if a trained model having a hierarchical relationship with a plurality of trained models is included in the candidates, the selection unit 210 selects a plurality of trained models having a hierarchical relationship by comparing the degrees of conformity of the plurality of candidates including the trained model having a hierarchical relationship with a plurality of trained models.

According to the present exemplary embodiment, it is possible to select a plurality of trained models having an appropriate hierarchical relationship even in a case where a plurality of trained models having a plurality of hierarchical relationships is selected as candidates.

A computer program for implementing the functions according to the above-described exemplary embodiments can be supplied to a computer via a network or a storage medium (not illustrated) and the computer can be caused to execute the computer program. The computer program is a computer program for causing the computer to execute the above-described information processing method. In other words, the computer program is a program for causing the computer to implement the functions of the information processing apparatus 130. The storage medium stores the computer program.

OTHER EMBODIMENTS

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-169032, filed Oct. 6, 2020, which is hereby incorporated by reference herein in its entirety.

What is claimed is:

1. An information processing apparatus comprising:
a storage unit configured to store a plurality of trained models including a first trained model for classifying inference target image data into a class belonging to a first class hierarchy, and a second trained model for classifying inference target image data into a class belonging to a second class hierarchy lower than the first class hierarchy;
an acquisition unit configured to acquire information about inference;
a selection unit configured to select a plurality of trained models having a hierarchical relationship and performing inference, on inference target image data, in order from a trained model corresponding to a higher class hierarchy from among the stored plurality of trained models, based on the acquired information about inference; and
a notification unit configured to provide a notification of the selected plurality of trained models.

2. The information processing apparatus according to claim 1, wherein the information about inference is information indicating at least one of an inference target, an inference purpose, or a class.

3. The information processing apparatus according to claim 1, further comprising an inference unit configured to perform inference using the selected plurality of trained models having the hierarchical relationship.

4. The information processing apparatus according to claim 3, wherein the inference unit performs the inference starting from a trained model for classifying the medical image data into a class belonging to a highest class hierarchy among the selected plurality of trained models having the hierarchical relationship.

5. The information processing apparatus according to claim 1, wherein the selection unit calculates a degree of conformity with a trained model corresponding to each class hierarchy, based on the information about inference, and selects the plurality of trained models based on the calculated degree of conformity.

6. The information processing apparatus according to claim 5, wherein the selection unit selects the plurality of trained models from among trained models with the calculated degree of conformity being greater than a predetermined value.

7. The information processing apparatus according to claim 6, wherein the selection unit selects a trained model corresponding to a lowest class hierarchy and a trained model that corresponds to a class hierarchy higher than the lowest class hierarchy and has the hierarchical relationship with the trained model corresponding to the lowest class hierarchy, from among the trained models with the calculated degree of conformity being greater than the predetermined value.

8. The information processing apparatus according to claim 6, wherein the selection unit selects a trained model corresponding to a highest class hierarchy and a trained model that corresponds to a class hierarchy lower than the highest class hierarchy and has the hierarchical relationship with the trained model corresponding to the highest class hierarchy, from among the trained models with the calculated degree of conformity being greater than the predetermined value.

9. The information processing apparatus according to claim 6, wherein the selection unit selects a trained model corresponding to a highest class hierarchy and a trained model corresponding to a lowest class hierarchy from among the trained models with the calculated degree of conformity being greater than the predetermined value, and in a case where there is another class hierarchy between the highest class hierarchy and the lowest class hierarchy, the selection unit further selects a trained model corresponding to the other class hierarchy.

10. The information processing apparatus according to claim 1, wherein the acquisition unit further acquires selection information about the trained models, and the selection unit selects the plurality of trained models having the hierarchical relationship, based on the selection information.

11. The information processing apparatus according to claim 5, wherein the selection unit calculates the degree of conformity by using a trained model for classifying the class belonging to the first class hierarchy and the class belonging to the second class hierarchy.

12. An information processing method comprising:
acquiring information about inference;
selecting a plurality of trained models having a hierarchical relationship and performing inference, on inference target image data, in order from a trained model corresponding to a higher class hierarchy based on the acquired information about inference; and
providing a notification of the selected plurality of trained models.

13. A non-transitory computer-readable storage medium storing a program for causing a computer to execute the information processing method according to claim 12.

14. An information processing system comprising:
an information processing apparatus including a storage unit configured to store a plurality of trained models including a first trained model for classifying inference target image data into a class belonging to a first class hierarchy, and a second trained model for classifying inference target image data into a class belonging to a second class hierarchy lower than the first class hierarchy; and
an information terminal configured to communicate with the information processing apparatus via a network, wherein the information processing apparatus includes:
an acquisition unit configured to acquire information about inference;
a selection unit configured to select a plurality of trained models having a hierarchical relationship and performing inference, on inference target image data, in order from a trained model corresponding to a higher class hierarchy from among the stored plurality of trained models, based on the acquired information about inference; and
a notification unit configured to notify the information terminal of the selected plurality of trained models.

15. The information processing system according to claim 14, wherein the information terminal includes:
a display unit configured to display the plurality of trained models that the information terminal is notified of by the notification unit; and
an operation unit configured to receive an operation to select a trained model to be used in performing the inference, based on the plurality of trained models that the information terminal is notified of by the notification unit.

16. The information processing system according to claim 15, wherein the acquisition unit in the information processing apparatus acquires selection information about the trained model selected on the operation unit, and the selection unit selects the plurality of trained models having the hierarchical relationship, based on the selection information.

17. The information processing apparatus according to claim 3, wherein the inference unit performs first inference using the first trained model corresponding to the first class hierarchy among the stored plurality of trained models having the hierarchical relationship and performs second inference using a trained model corresponding to a class hierarchy lower than the first class hierarchy among the stored plurality of trained models having the hierarchical relationship.

18. The information processing apparatus according to claim 17, wherein based on a result of the first inference, the inference unit performs the second inference.

19. The information processing apparatus according to claim 18, wherein the inference unit performs the second inference by using an input that is based on the result of the first inference.

20. The information processing apparatus according to claim 1, wherein the inference target image data is medical image data.

* * * * *